(12) United States Patent
Quarmby et al.

(10) Patent No.: US 10,242,850 B2
(45) Date of Patent: Mar. 26, 2019

(54) OFFLINE MASS CALIBRATION

(71) Applicant: Thermo Finnigan LLC, San Jose, CA (US)

(72) Inventors: Scott T. Quarmby, Round Rock, TX (US); George B. Guckenberger, Austin, TX (US)

(73) Assignee: THERMO FINNIGAN LLC, San Jose, CA (US)

( * ) Notice: Subject to any disclaimer, the term of this patent is extended or adjusted under 35 U.S.C. 154(b) by 383 days.

(21) Appl. No.: 15/079,476

(22) Filed: Mar. 24, 2016

(65) Prior Publication Data

US 2016/0284527 A1   Sep. 29, 2016

Related U.S. Application Data

(60) Provisional application No. 62/138,239, filed on Mar. 25, 2015.

(51) Int. Cl.
*H01J 49/00* (2006.01)
*G01N 30/72* (2006.01)
(Continued)

(52) U.S. Cl.
CPC ...... *H01J 49/0009* (2013.01); *G01N 30/7206* (2013.01); *G01N 30/7233* (2013.01);
(Continued)

(58) Field of Classification Search
CPC combination set(s) only.
See application file for complete search history.

(56) References Cited

U.S. PATENT DOCUMENTS

2002/0033447 A1   3/2002   Bowdler
2009/0050796 A1   2/2009   Hager
(Continued)

FOREIGN PATENT DOCUMENTS

CN    1898674 A     1/2007
CN    103262204 A   8/2013
(Continued)

OTHER PUBLICATIONS

Burton et al., "Exact Mass Measurements Using a 7 Tesla Fourier Transform Ion Cyclotron Resonance Mass Spectrometer in a Good laboratory Practices-Regulated Environment," J Am. Soc. Mass Spec., 1999, 10, pp. 1291-1297.
(Continued)

*Primary Examiner* — Phillip A Johnston
*Assistant Examiner* — Hsien Tsai
(74) *Attorney, Agent, or Firm* — David A. Schell (57) ABSTRACT

A method includes producing ions from one or more calibrant species and delivering the ions to a mass analyzer, and measuring a first set of mass related physical values for the ions from the one or more calibrant species. The method further includes producing ions from a sample and delivering the ions to a mass analyzer, and measuring a second mass related physical value for a first sample ion species. The first sample ion species has a mass-to-charge ratio outside of the range of the mass-to-charge ratios of the calibrant ion species. Additionally, the method includes calculating a calibration curve based on the first set of mass related physical values and second mass related physical value, and modifying at least one instrument parameter based on the calibration curve.

27 Claims, 10 Drawing Sheets

(51) Int. Cl.
  *H01J 49/04* (2006.01)
  *H01J 49/40* (2006.01)
  *H01J 49/42* (2006.01)
(52) U.S. Cl.
  CPC .............. *H01J 49/04* (2013.01); *H01J 49/40* (2013.01); *H01J 49/4225* (2013.01)

(56) References Cited

U.S. PATENT DOCUMENTS

| | | |
|---|---|---|
| 2009/0212205 A1* | 8/2009 | Thomson ............ H01J 49/0036 250/282 |
| 2010/0059666 A1 | 3/2010 | Remes et al. |
| 2010/0120156 A1 | 5/2010 | Garner et al. |
| 2011/0012013 A1 | 1/2011 | Remes et al. |
| 2013/0214146 A1 | 8/2013 | Okumura |
| 2013/0240724 A1 | 9/2013 | Guna |

FOREIGN PATENT DOCUMENTS

| | | |
|---|---|---|
| CN | 103282770 A | 9/2013 |
| CN | 104160472 A | 11/2014 |
| EP | 1193731 A1 | 4/2002 |
| EP | 1347492 A2 | 9/2003 |
| GB | 2401721 A | 11/2004 |
| GB | 2513463 A | 10/2014 |
| WO | 00/70649 A1 | 11/2000 |
| WO | 2006/129083 A2 | 12/2006 |
| WO | 2009023946 A1 | 2/2009 |
| WO | 2013/104004 A1 | 7/2013 |
| WO | 2014135866 A1 | 9/2014 |

OTHER PUBLICATIONS

Kozhinov, et al., "Iterative Method for Mass Spectra Recalibration via Empirical Estimation of the Mass Calibration Function for Fourier Transform Mass Spectrometry-Based Petroleomics", Anal. Chem. 2013, 85, pp. 6437-6445.

Makarov, et al., "Performance Evaluation of a Hybrid Linear Ion Trap/Orbitrap Mass Spectrometer", Anal. Chem. 2006, 78, pp. 2113-2120.

* cited by examiner

OFFLINE MASS CALIBRATION

FIELD

The present disclosure generally relates to the field of mass spectrometry including systems and methods for mass calibration.

INTRODUCTION

Mass spectrometry relies upon the measurement of physical values that can be related to the mass-to-charge ratio (m/z) to determine a mass of an ionic species or a compound within a sample. High mass accuracy requires calibration of the measured physical values against species of known m/z or mass. Calibration is generally accomplished with the use of a calibration mixture that produces multiple ionic species of known m/z. However, the choice of ions suitable for use in a calibration mixture may be limited.

From the foregoing it will be appreciated that a need exists for improved calibration methods for mass spectrometry.

SUMMARY

In a first aspect, a method can include producing ions from one or more calibrant species and delivering the ions to a mass analyzer, and measuring a first set of mass related physical values for the ions from the one or more calibrant species. The method can further include producing ions from a sample and delivering the ions to a mass analyzer, and measuring a second mass related physical value for a first sample ion species. The first sample ion species can have a mass-to-charge ratio outside of the range of the mass-to-charge ratios of the calibrant ion species. Additionally, the method can include calculating a calibration curve based on the first set of mass related physical values for the plurality calibrant ion species and second mass related physical value for the first sample ion species, and modifying at least one instrument parameter based on the calibration curve.

In various embodiments of the first aspect, the mass analyzer can include a Fourier transform mass analyzer. In specific embodiments, the instrument parameter can be selected from the group consisting of a coefficient relating m/z to ion frequency, a frequency range for an image current, a digitizing rate, a filter bandwidth for an image current, and any combination thereof.

In various embodiments of the first aspect, the mass analyzer can include a quadrupole mass analyzer or a quadrupole ion trap mass analyzer. In specific embodiments, the instrument parameter can be selected from the group consisting of an RF voltage, a DC voltage, and any combination thereof.

In various embodiments of the first aspect, the mass analyzer can include a time-of-flight mass analyzer. In specific embodiments, the instrument parameter can be selected from the group consisting of a coefficient relating m/z to flight time, an acquisition time window, a flight tube clearing pulse time, and any combination thereof.

In various embodiments of the first aspect, the sample can be provided by a gas chromatographic instrument.

In various embodiments of the first aspect, the sample can be provided by a liquid chromatographic instrument.

In various embodiments of the first aspect, the method can further include providing a second sample including a second sample ion species to the mass spectrometer; operating the mass spectrometer using the modified instrument parameter from the calibration; and measuring a third mass related physical value for the second sample ion species.

In specific embodiments, the method can further include shifting the calibration curve based on a measured mass-to-charge ratio of a third sample ion species within the second sample to account for scan specific drifts in the calibration curve, wherein the instrument parameter is not changed based on the shifting of the calibration curve. In specific embodiments, the second sample ion species can have a mass-to-charge ratio within the range of the mass-to-charge ratio of the first sample ion species and the mass-to-charge ratio of at least one of the calibrant ion species.

In various embodiments of the first aspect, the first sample ion species can have a mass-to-charge ratio above the range of the mass-to-charge ratios of the calibrant ion species.

In various embodiments of the first aspect, the first sample ion species can have a mass-to-charge ratio below the range of the mass-to-charge ratios of the calibrant ion species.

In a second aspect, a mass spectrometer can include an ion source configured to form ions; a mass analyzer configured to measure a mass related physical value for an ion; and a controller. The controller can be configured to obtain a first set of mass related physical values for ions from the one or more calibrant species; obtain a second mass related physical value for a first sample ion species; calculate a calibration curve based on the first set of mass related physical values, the second mass related physical value, and known mass-to-charge ratios of ions from the one or more calibrant species and the first sample ion species; and modify the operation of the mass analyzer based on the calibration curve.

In various embodiments of the second aspect, the mass analyzer can include a Fourier transform mass analyzer. In specific embodiments, modifying the operation of the mass analyzer can include modifying a coefficient relating m/z to ion frequency, a frequency range for an image current, a digitizing rate, a filter bandwidth for an image current, and any combination thereof.

In various embodiments of the second aspect, the mass analyzer can include a quadrupole mass analyzer or a quadrupole ion trap mass analyzer. In specific embodiments, modifying the operation of the mass analyzer can include modifying an RF voltage, a DC voltage, or any combination thereof.

In various embodiments of the second aspect, the mass analyzer can include a time-of-flight mass analyzer. In specific embodiments, modifying the operation of the mass analyzer can include modifying a coefficient relating m/z to flight time, an acquisition time window, a flight tube clearing pulse time, or any combination thereof.

In various embodiments of the second aspect, the mass spectrometer can further include a gas chromatograph for supplying a sample to the ion source.

In various embodiments of the second aspect, the mass spectrometer can further include a liquid chromatograph for supplying a sample to the ion source.

In various embodiments of the second aspect, the controller can be further configured to operate the ion source to provide a second sample including a second sample ion species to the mass spectrometer; operate the mass spectrometer using the modified instrument parameter from the calibration; and obtain a third set of mass related physical values for the second sample ion species. In specific embodiments, the controller can be further configured to shift the calibration curve based on a measured mass-to-charge ratio of a third sample ion species within the second sample to account for scan specific drift in the calibration curve, wherein the operation of the mass analyzer is not changed based on the shifting of the calibration curve.

In various embodiments of the second aspect, first sample ion species can have a mass-to-charge ratio above the range of the mass-to-charge ratios of the calibrant ion species.

In various embodiments of the second aspect, first sample ion species can have a mass-to-charge ratio below the range of the mass-to-charge ratios of the calibrant ion species.

DRAWINGS

For a more complete understanding of the principles disclosed herein, and the advantages thereof, reference is now made to the following descriptions taken in conjunction with the accompanying drawings, in which.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DESCRIPTION OF VARIOUS EMBODIMENTS

Embodiments of systems and methods for mass calibration are described herein.

The section headings used herein are for organizational purposes only and are not to be construed as limiting the described subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless described otherwise, all technical and scientific terms used herein have a meaning as is commonly understood by one of ordinary skill in the art to which the various embodiments described herein belongs.

It will be appreciated that there is an implied "about" prior to the temperatures, concentrations, times, pressures, flow rates, cross-sectional areas, etc. discussed in the present teachings, such that slight and insubstantial deviations are within the scope of the present teachings. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the present teachings.

As used herein, "a" or "an" also may refer to "at least one" or "one or more." Also, the use of "or" is inclusive, such that the phrase "A or B" is true when "A" is true, "B" is true, or both "A" and "B" are true. Further, unless otherwise required by context, singular terms shall include pluralities and plural terms shall include the singular.

A "system" sets forth a set of components, real or abstract, comprising a whole where each component interacts with or is related to at least one other component within the whole.

Mass Spectrometry Platforms

Figure 1:
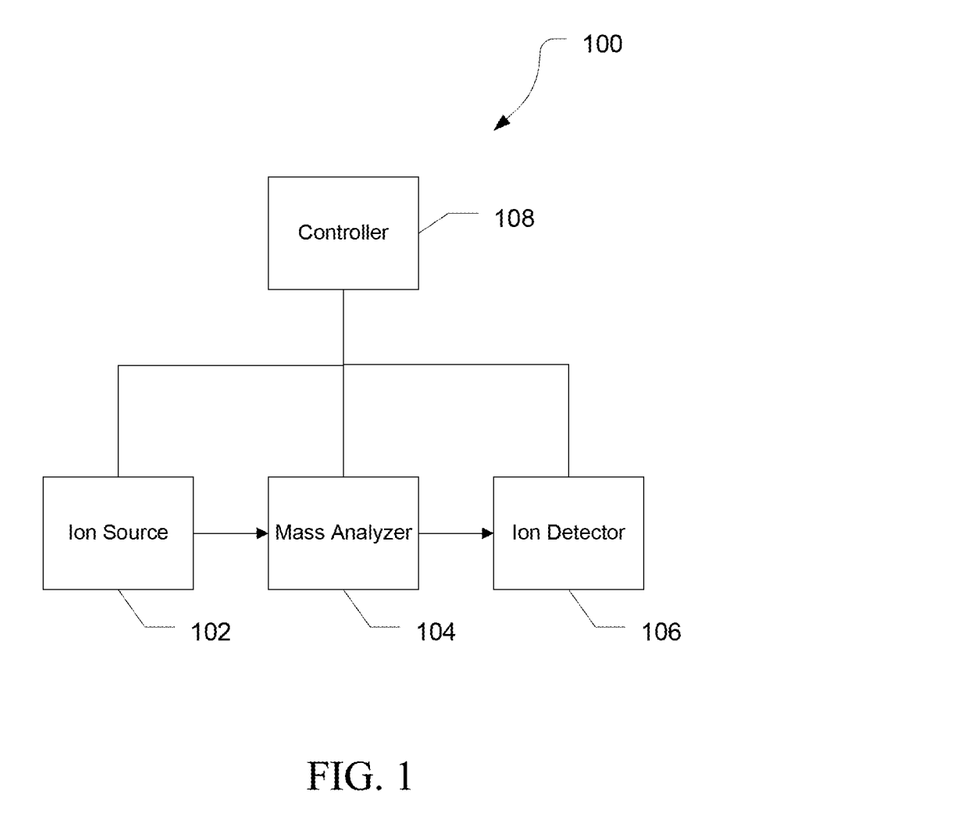
FIG. 1 is a block diagram of an exemplary mass spectrometry system, in accordance with various embodiments.

Various embodiments of mass spectrometry platform 100 can include components as displayed in the block diagram of FIG. 1. In various embodiments, elements of FIG. 1 can be incorporated into mass spectrometry platform 100. According to various embodiments, mass spectrometer 100 can include an ion source 102, a mass analyzer 104, an ion detector 106, and a controller 108.

In various embodiments, the ion source 102 generates a plurality of ions from a sample. The ion source can include, but is not limited to, a matrix assisted laser desorption/ionization (MALDI) source, electrospray ionization (ESI) source, atmospheric pressure chemical ionization (APCI) source, atmospheric pressure photoionization source (APPI), inductively coupled plasma (ICP) source, electron ionization source, chemical ionization source, photoionization source, glow discharge ionization source, thermospray ionization source, and the like.

In various embodiments, the mass analyzer 104 can separate ions based on a mass-to-charge ratio of the ions. For example, the mass analyzer 104 can include a quadrupole mass filter analyzer, a quadrupole ion trap analyzer, a time-of-flight (TOF) analyzer, an electrostatic trap (e.g., Orbitrap) mass analyzer, Fourier transform ion cyclotron resonance (FT-ICR) mass analyzer, and the like. In various embodiments, the mass analyzer 104 can also be configured to fragment the ions using collision induced dissociation (CID) electron transfer dissociation (ETD), electron capture dissociation (ECD), photo induced dissociation (PID), surface induced dissociation (SID), and the like, and further separate the fragmented ions based on the mass-to-charge ratio.

In various embodiments, the ion detector 106 can detect ions. For example, the ion detector 106 can include an electron multiplier, a Faraday cup, and the like. Ions leaving the mass analyzer can be detected by the ion detector. In various embodiments, the ion detector can be quantitative, such that an accurate count of the ions can be determined.

In various embodiments, the controller 108 can communicate with the ion source 102, the mass analyzer 104, and the ion detector 106. For example, the controller 108 can configure the ion source or enable/disable the ion source. Additionally, the controller 108 can configure the mass analyzer 104 to select a particular mass range to detect. Further, the controller 108 can adjust the sensitivity of the ion detector 106, such as by adjusting the gain. Additionally, the controller 108 can adjust the polarity of the ion detector 106 based on the polarity of the ions being detected. For example, the ion detector 106 can be configured to detect positive ions or be configured to detected negative ions.

Calibration Method

Figure 2A:
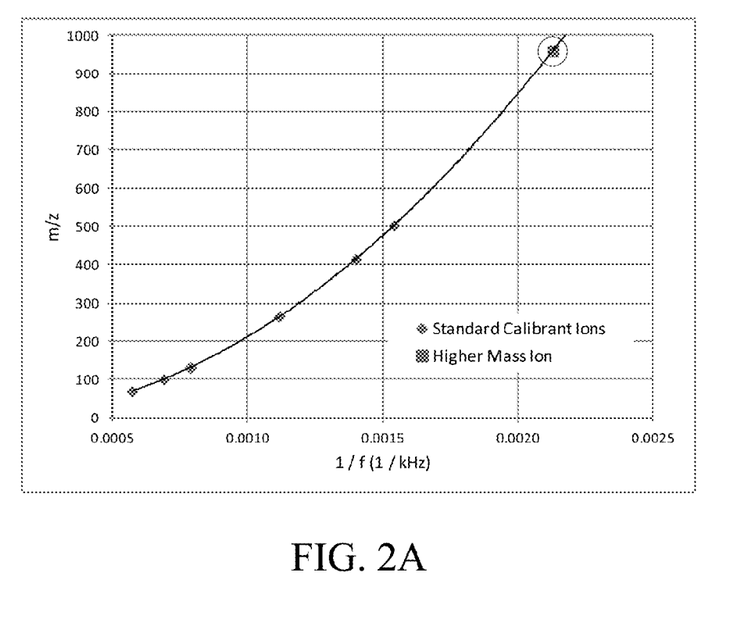
FIGS. 2A and 2B are graphs illustrating an extrapolation error when only low mass ions are used for calibration, in accordance with various embodiments.
Figure 2B:
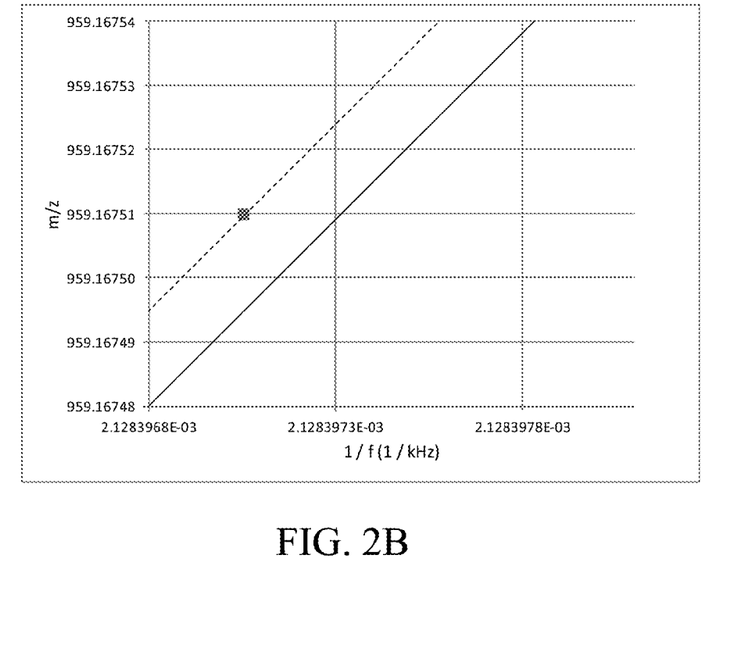

FIG. 2A is a graph illustrating a calibration curve when using only low mass ions from a calibrant mixture and when using the low mass ions in a calibration mixture in combination with a high mass ion from a sample. FIG. 2B is an enlargement of the circled region around the point corresponding to the high mass ion. The solid line is a fit of the standard calibrant ions to equation 3. The standard calibrant ions are 68.99466, 99.99306, 130.99147, 263.98656, 413.97698, and 501.97059. At m/z 959.16751, the fit is significantly off. The dashed line is a fit of the standard calibrant ions plus the higher mass ion to equation 3. This fit has improved accuracy over the range from low mass to high mass.

Figure 3:
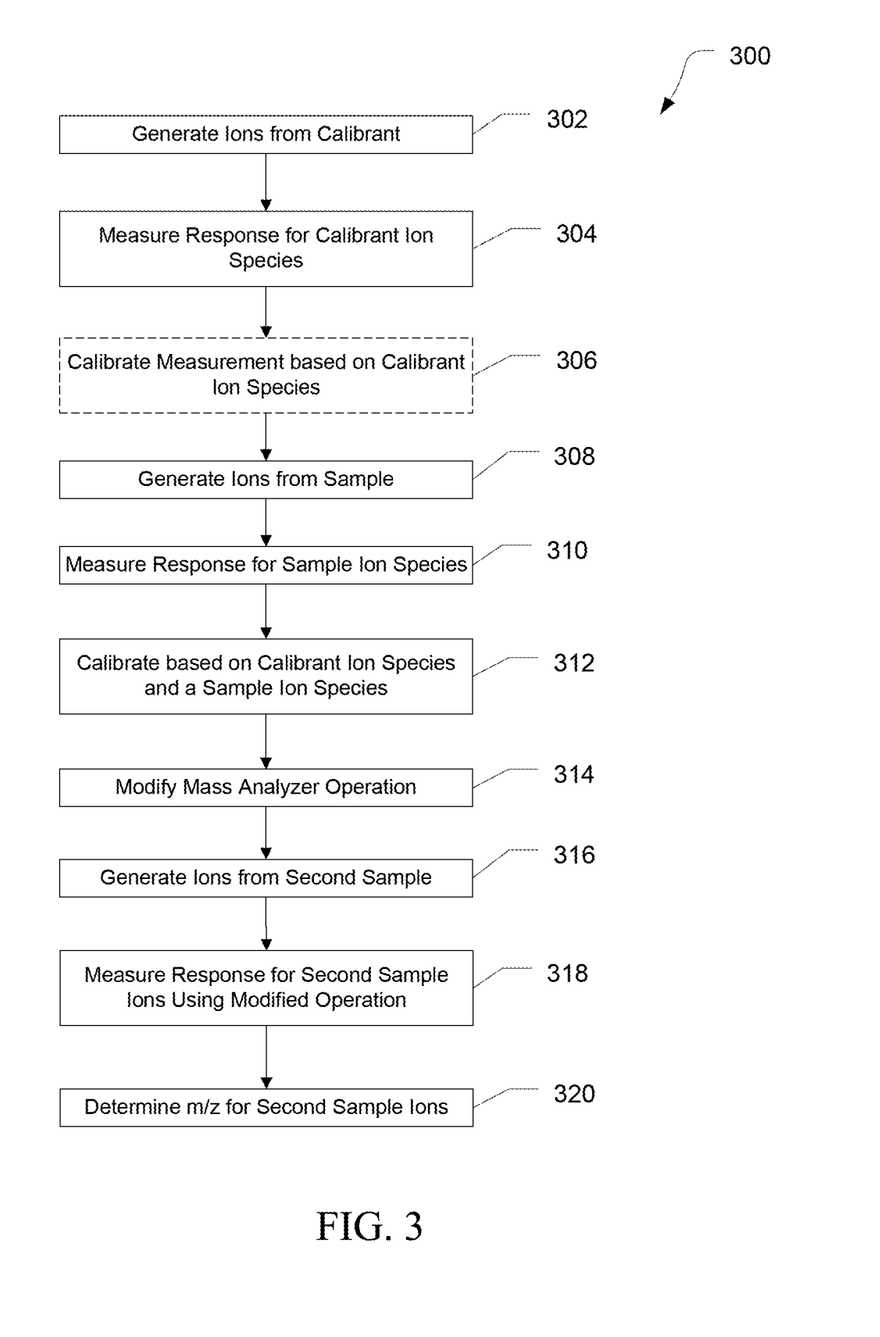
FIG. 3 is a flow diagram of an exemplary method for calibrating a mass analyzer, in accordance with various embodiments.

FIG. 3 is a flow diagram for calibrating a mass analyzer, such as mass analyzer 104 of FIG. 1. At 302, ions can be generated from a calibrant mixture. In various embodiments, the calibrant mixture can include a multiple species of known mass which can cover a range of masses. The ions of the calibrant mixture can be analyzed by the mass analyzer at 304 and a set of physical values related to the m/z can be measured. Depending on the type of mass analyzer, the mass related physical value can be a frequency, a time, a voltage, or the like.

In various embodiments, when using a Fourier transform mass analyzer, such as an Orbitrap or a Fourier Transform Ion Cyclotron Resonance (FTICR) mass analyzer, the m/z ratio can be related to a measured frequency f of an induced current caused by the oscillation of the ion in the mass analyzer. The relationship can be described using Equation 1, 2, or 3 for an Orbitrap or Equation 4 for a FTICR mass analyzer.

$$\frac{m}{z} = \frac{A}{f^2} \qquad 1.$$

$$\frac{m}{z} = \frac{A}{f^3} + \frac{B}{f^2} \qquad 2.$$

$$\frac{m}{z} = \frac{A}{f^3} + \frac{B}{f^2} + \frac{C}{f} + D \qquad 3.$$

$$\frac{m}{z} = \frac{A}{f} + \frac{B}{f^2} \qquad 4.$$

In various embodiments, when using a quadrupole mass analyzer, such as a quadrupole mass filter or a quadrupole ion trap, the m/z ratio can be related to a voltage V applied to the quadrupole. Additionally, there can be a time delay between when a voltage is set and when the voltage is applied to the quadrupole and the ions respond to the change in the field. When scanning across a mass range, it may be necessary to correct for the response delay. In various embodiments, this can be accomplished by introducing a voltage offset B which may be a function of scan rate. The relationship can be described using Equation 5 and the correction for the response delay can be described using Equation 6.

$$\frac{m}{z} = \frac{e}{2\pi^2 f^2 r_o^2} V \qquad 5.$$

$$\frac{m}{z} = A \cdot V + B \qquad 6.$$

In various embodiments, when using a time-of-flight mass analyzer the m/z ratio can be related to a time t it takes for the ion to travel the flight path. The relationship can be described using Equations 7 and 8.

$$\frac{m}{z} = \frac{2eV_s}{L^2} t^2 \qquad 7.$$

$$\frac{m}{z} = A \cdot t^2 + B \qquad 8.$$

In various embodiments, a calibration for the physical value can optionally be determined from the measured values and the known masses, as indicated at 306.

At 308, ions can be generated from a sample containing at least one species of known mass. The species of known mass can have a mass outside of the range covered by the calibrant, either lower or higher or even in between. In various embodiments, the sample can be a calibration sample used to calibrate a chromatograph, such as a gas chromatograph or a liquid chromatograph. In this way, calibration of the mass analyzer can occur concurrently with calibration of the chromatograph. In other embodiments, calibration of the chromatograph may occur less frequently than calibration of the mass analyzer, and a species known to be in a sample or spiked into a sample can be used.

At 310, the mass related physical value can be measured for the ions within the sample, including the species of known mass. At 312, a calibration curve can be calculated for the mass related physical value. The calibration can use the set of mass related physical values measured for the calibrant ion species and the mass related physical value measured for the species of known mass in the sample. In various embodiments, the calibration curve can be used to determine masses of unknown ions from the measured mass related physical value with an error of not greater than about 10 ppm, such as not greater than about 5 ppm, such as not greater than about 2 ppm, or even not greater than about 1 ppm.

At 314, the operation of the mass analyzer can be modified based on the calibration curve. In embodiments, when using a Fourier transform mass analyzer, a coefficient relating m/z to ion frequency, a frequency range for an image current, a digitizing rate, a filter bandwidth for an image current, or any combination thereof can be modified based on the calibration curve. In other embodiments, when using a quadrupole mass analyzer or a quadrupole ion trap mass analyzer, an RF voltage, a DC voltage, or any combination thereof can be modified based on the calibration curve. In further embodiments, when using a time-of-flight mass analyzer, a coefficient relating m/z to flight time, an acquisition time window, a flight tube clearing pulse time, or any combination thereof can be modified based on the calibration curve.

At 316, ions can be generated from a second sample, and at 318, the mass related physical value can be measured using the modified operation of the mass analyzer.

At 320, the mass of the ions in the second sample can be determined based on the calibration curve. In various embodiments, a lock mass can be used to modify the calibration curve to further improve mass accuracy. The lock mass can be derived from a species of known mass within the second sample and can be used to shift or rotate the curve to account for run specific changes in the operation of the mass analyzer. Various factors can contribute to run specific alterations to the measured mass related physical value, such as a temperature of various components of the mass analyzer, a total number of ions within the mass analyzer, and other factors. The use of the lock mass can correct for these run specific affects without altering the operation of the mass analyzer, and can be applied while the data is collected for the sample and before saving the data, or can be applied after the data is collected for the sample.

Computer-Implemented System

Figure 4:
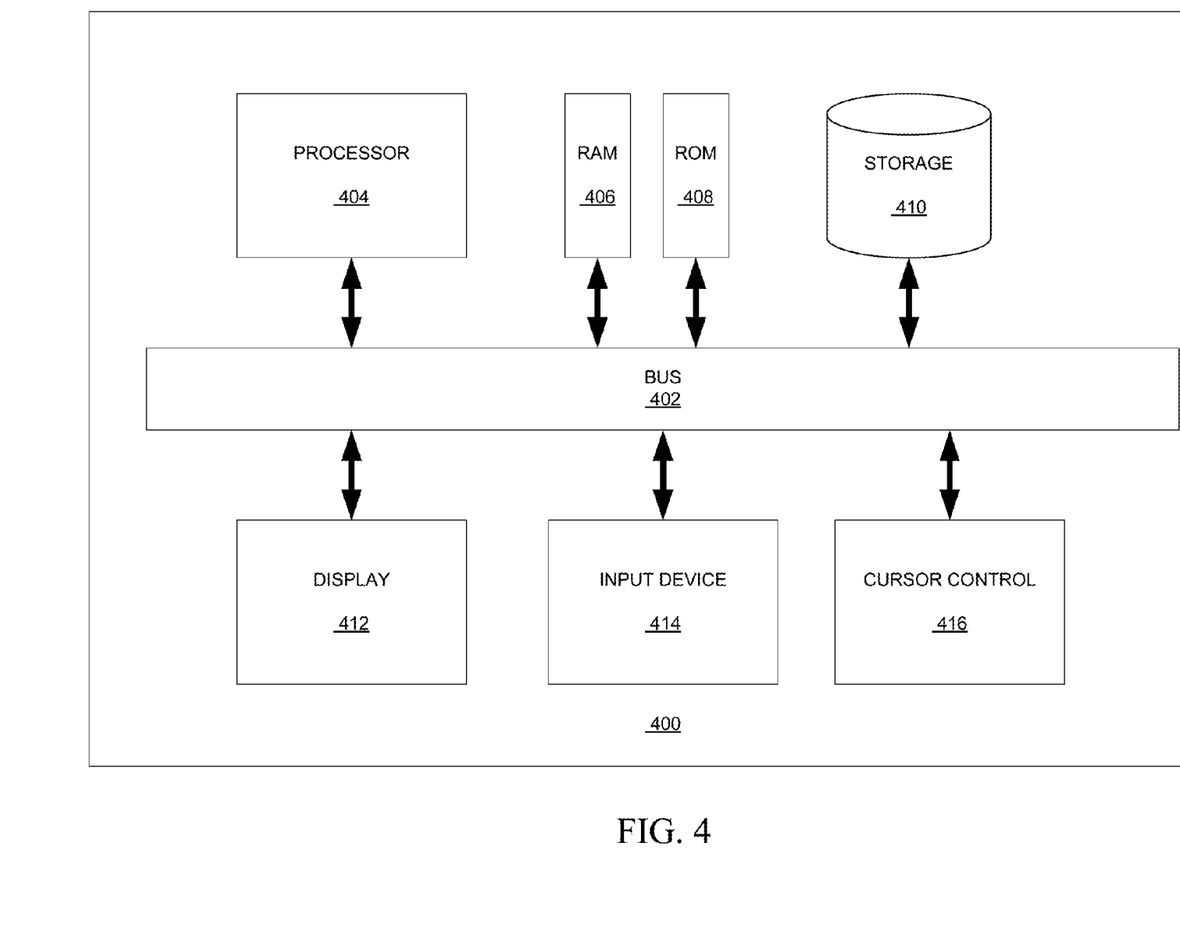
FIG. 4 is a flow block illustrating an exemplary computer system, in accordance with various embodiments.

FIG. 4 is a block diagram that illustrates a computer system 400, upon which embodiments of the present teachings may be implemented as which may incorporate or communicate with a system controller, for example controller 108 shown in FIG. 1, such that the operation of components of the associated mass spectrometer may be adjusted in accordance with calculations or determinations made by computer system 400. In various embodiments, computer system 400 can include a bus 402 or other communication mechanism for communicating information, and a processor 404 coupled with bus 402 for processing information. In various embodiments, computer system 400 can also include a memory 406, which can be a random access memory (RAM) or other dynamic storage device, coupled to bus 402 for determining base calls, and instructions to be executed by processor 404. Memory 406 also can be used for storing temporary variables or other intermediate information during execution of instructions to be executed by processor 404. In various embodiments, computer system 400 can further include a read only memory (ROM) 408 or other static storage device coupled to bus 402 for storing static information and instructions for processor 404. A storage device 410, such as a magnetic disk or optical disk, can be provided and coupled to bus 402 for storing information and instructions.

In various embodiments, processor 404 can include a plurality of logic gates. The logic gates can include AND gates, OR gates, NOT gates, NAND gates, NOR gates, EXOR gates, EXNOR gates, or any combination thereof. An AND gate can produce a high output only if all the inputs are high. An OR gate can produce a high output if one or more of the inputs are high. A NOT gate can produce an inverted version of the input as an output, such as outputting a high value when the input is low. A NAND (NOT-AND) gate can produce an inverted AND output, such that the output will be high if any of the inputs are low. A NOR (NOT-OR) gate can produce an inverted OR output, such that the NOR gate output is low if any of the inputs are high. An EXOR (Exclusive-OR) gate can produce a high output if either, but not both, inputs are high. An EXNOR (Exclusive-NOR) gate can produce an inverted EXOR output, such that the output is low if either, but not both, inputs are high.

TABLE 1

Logic Gates Truth Table

| INPUTS | | OUTPUTS | | | | | | |
|---|---|---|---|---|---|---|---|---|
| A | B | NOT A | AND | NAND | OR | NOR | EXOR | EXNOR |
| 0 | 0 | 1 | 0 | 1 | 0 | 1 | 0 | 1 |
| 0 | 1 | 1 | 0 | 1 | 1 | 0 | 1 | 0 |
| 1 | 0 | 0 | 0 | 1 | 1 | 0 | 1 | 0 |
| 1 | 1 | 0 | 1 | 0 | 1 | 0 | 0 | 1 |

One of skill in the art would appreciate that the logic gates can be used in various combinations to perform comparisons, arithmetic operations, and the like. Further, one of skill in the art would appreciate how to sequence the use of various combinations of logic gates to perform complex processes, such as the processes described herein.

In an example, a 1-bit binary comparison can be performed using a XNOR gate since the result is high only when the two inputs are the same. A comparison of two multi-bit values can be performed by using multiple XNOR gates to compare each pair of bits, and the combining the output of the XNOR gates using and AND gates, such that the result can be true only when each pair of bits have the same value. If any pair of bits does not have the same value, the result of the corresponding XNOR gate can be low, and the output of the AND gate receiving the low input can be low.

In another example, a 1-bit adder can be implemented using a combination of AND gates and XOR gates. Specifically, the 1-bit adder can receive three inputs, the two bits to be added (A and B) and a carry bit (Cin), and two outputs, the sum (S) and a carry out bit (Cout). The Cin bit can be set to 0 for addition of two one bit values, or can be used to couple multiple 1-bit adders together to add two multi-bit values by receiving the Cout from a lower order adder. In an exemplary embodiment, S can be implemented by applying the A and B inputs to a XOR gate, and then applying the result and Cin to another XOR gate. Cout can be implemented by applying the A and B inputs to an AND gate, the result of the A-B XOR from the SUM and the Cin to another AND, and applying the input of the AND gates to a XOR gate.

TABLE 2

1-bit Adder Truth Table

| INPUTS | | | OUTPUTS | |
|---|---|---|---|---|
| A | B | Cin | S | Cout |
| 0 | 0 | 0 | 0 | 0 |
| 1 | 0 | 0 | 0 | 1 |
| 0 | 1 | 0 | 0 | 1 |
| 1 | 1 | 0 | 1 | 0 |
| 0 | 0 | 1 | 0 | 1 |
| 1 | 0 | 1 | 1 | 0 |
| 0 | 1 | 1 | 1 | 0 |
| 1 | 1 | 1 | 1 | 1 |

In various embodiments, computer system 400 can be coupled via bus 402 to a display 412, such as a cathode ray tube (CRT) or liquid crystal display (LCD), for displaying information to a computer user. An input device 414, including alphanumeric and other keys, can be coupled to bus 402 for communicating information and command selections to processor 404. Another type of user input device is a cursor control 416, such as a mouse, a trackball or cursor direction keys for communicating direction information and command selections to processor 404 and for controlling cursor movement on display 412. This input device typically has two degrees of freedom in two axes, a first axis (i.e., x) and a second axis (i.e., y), that allows the device to specify positions in a plane.

A computer system 400 can perform the present teachings. Consistent with certain implementations of the present teachings, results can be provided by computer system 400 in response to processor 404 executing one or more sequences of one or more instructions contained in memory 406. Such instructions can be read into memory 406 from another computer-readable medium, such as storage device 410. Execution of the sequences of instructions contained in memory 406 can cause processor 404 to perform the processes described herein. In various embodiments, instructions in the memory can sequence the use of various combinations of logic gates available within the processor to perform the processes describe herein. Alternatively hard-wired circuitry can be used in place of or in combination with software instructions to implement the present teachings. In various embodiments, the hard-wired circuitry can include the necessary logic gates, operated in the necessary sequence to perform the processes described herein. Thus implementations of the present teachings are not limited to any specific combination of hardware circuitry and software.

The term "computer-readable medium" as used herein refers to any media that participates in providing instructions to processor 404 for execution. Such a medium can take many forms, including but not limited to, non-volatile media, volatile media, and transmission media. Examples of non-volatile media can include, but are not limited to, optical or magnetic disks, such as storage device 410. Examples of volatile media can include, but are not limited to, dynamic memory, such as memory 406. Examples of transmission media can include, but are not limited to, coaxial cables, copper wire, and fiber optics, including the wires that comprise bus 402.

Common forms of non-transitory computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

In various embodiments, the methods of the present teachings may be implemented in a software program and applications written in conventional programming languages such as C, C++, C#, etc.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

The embodiments described herein, can be practiced with other computer system configurations including hand-held devices, microprocessor systems, microprocessor-based or programmable consumer electronics, minicomputers, mainframe computers and the like. The embodiments can also be practiced in distributing computing environments where tasks are performed by remote processing devices that are linked through a network.

It should also be understood that the embodiments described herein can employ various computer-implemented operations involving data stored in computer systems. These operations are those requiring physical manipulation of physical quantities. Usually, though not necessarily, these quantities take the form of electrical or magnetic signals capable of being stored, transferred, combined, compared, and otherwise manipulated. Further, the manipulations performed are often referred to in terms, such as producing, identifying, determining, or comparing.

Any of the operations that form part of the embodiments described herein are useful machine operations. The embodiments, described herein, also relate to a device or an apparatus for performing these operations. The systems and methods described herein can be specially constructed for the required purposes or it may be a general purpose computer selectively activated or configured by a computer program stored in the computer. In particular, various general purpose machines may be used with computer programs written in accordance with the teachings herein, or it may be more convenient to construct a more specialized apparatus to perform the required operations.

Certain embodiments can also be embodied as computer readable code on a computer readable medium. The computer readable medium is any data storage device that can store data, which can thereafter be read by a computer system. Examples of the computer readable medium include hard drives, network attached storage (NAS), read-only memory, random-access memory, CD-ROMs, CD-Rs, CD-RWs, magnetic tapes, and other optical and non-optical data storage devices. The computer readable medium can also be distributed over a network coupled computer systems so that the computer readable code is stored and executed in a distributed fashion.

Results

The mass analyzer is calibrated using MS Grade Perfluorotributylamine (PFTBA) from SynQuest Labs, Alachua, Fla. The PFTBA calibration compound produces ions having theoretical masses of 68.99466, 99.99306, 130.99147, 263.98656, 413.97698, and 501.97059. A mixture of bromobiphenyl ethers from tri- to deca- (from Sigma-Aldrich, St Louis, Mo.) is analyzed.

Figure 5:
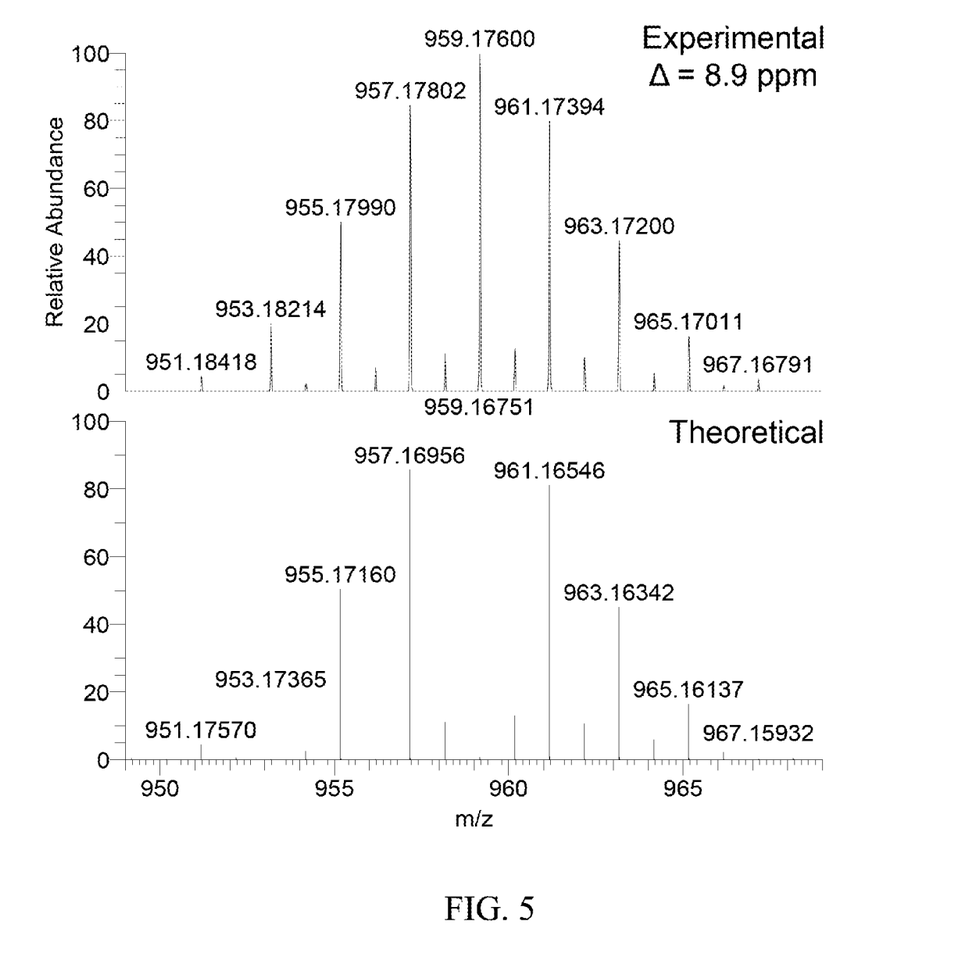
FIG. 5 is an exemplary comparison between a measured and theoretical m/z for a set of high mass ions when calibration is limited to low mass calibration ions.
Figure 6:
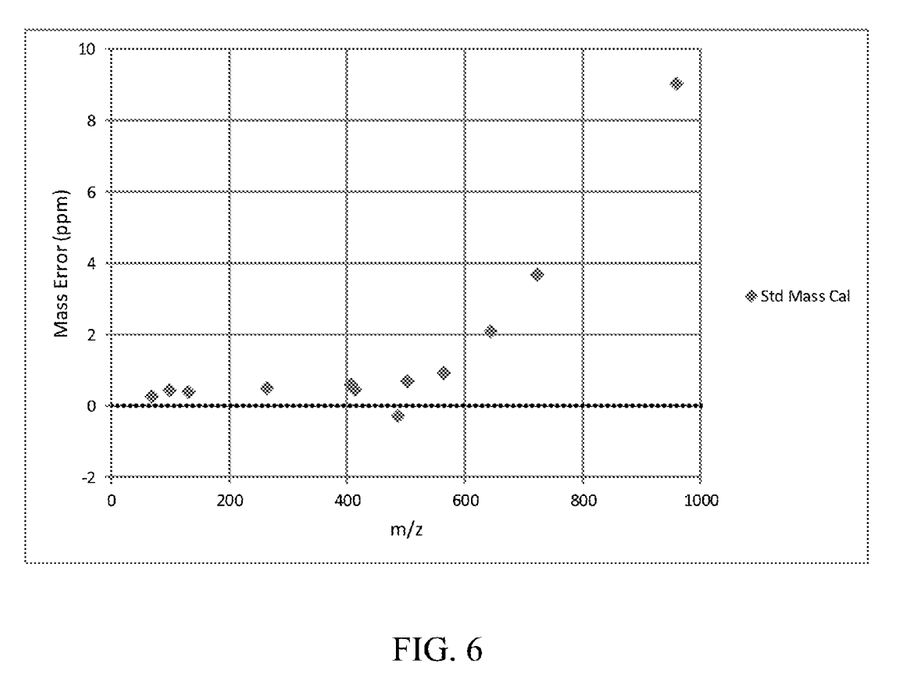
FIG. 6 is an exemplary graph of the mass errors as a function of m/z when calibration is limited to low mass calibration ions.

FIG. 5 shows an experimental mass spectrum of the bromobiphenyl ethers using the calibration derived from the PFTBA calibration compound as compared to a theoretical mass spectrum of the bromobiphenyl ethers. The error in the experimentally determined mass at m/z 959.16751 is 9 ppm. The data are tabulated in Table 1. FIG. 6 is a graph of the mass errors as a function of m/z ratio. The mass errors are stable within the m/z range covered by the PFTBA calibration compound, but increase as the m/z ratio moves further from the calibration range.

TABLE 1

|  | Theoretical m/z | Calculated m/z | Error |
|---|---|---|---|
| PFTBA | 68.9946612 | 68.99468 | 0.272484851 |
| PFTBA | 99.9930644 | 99.99311 | 0.456031629 |
| PFTBA | 130.9914676 | 130.99152 | 0.400026055 |
| PFTBA | 263.9865576 | 263.98669 | 0.501540689 |
| PFTBA | 413.9769768 | 413.97716 | 0.442536688 |
| PFTBA | 501.9705896 | 501.97093 | 0.678127379 |
| Tribromobiphenyl ether | 405.80211 | 405.80235 | 0.591421272 |
| Tetrabromobiphenyl ether | 485.71057 | 485.71043 | −0.288237499 |
| Pentabromobiphenyl ether | 563.62109 | 563.62161 | 0.922605646 |
| Hexabromobiphenyl ether | 643.52955 | 643.53089 | 2.082266463 |
| Heptabromobiphenyl ether | 721.44006 | 721.44271 | 3.673208832 |
| Decabromobiphenyl ether | 959.16751 | 959.17617 | 9.028662783 |
|  |  | RMS (ppm) | 2.915169831 |
|  |  | Max (ppm) | 9.028662783 |

Figure 7:
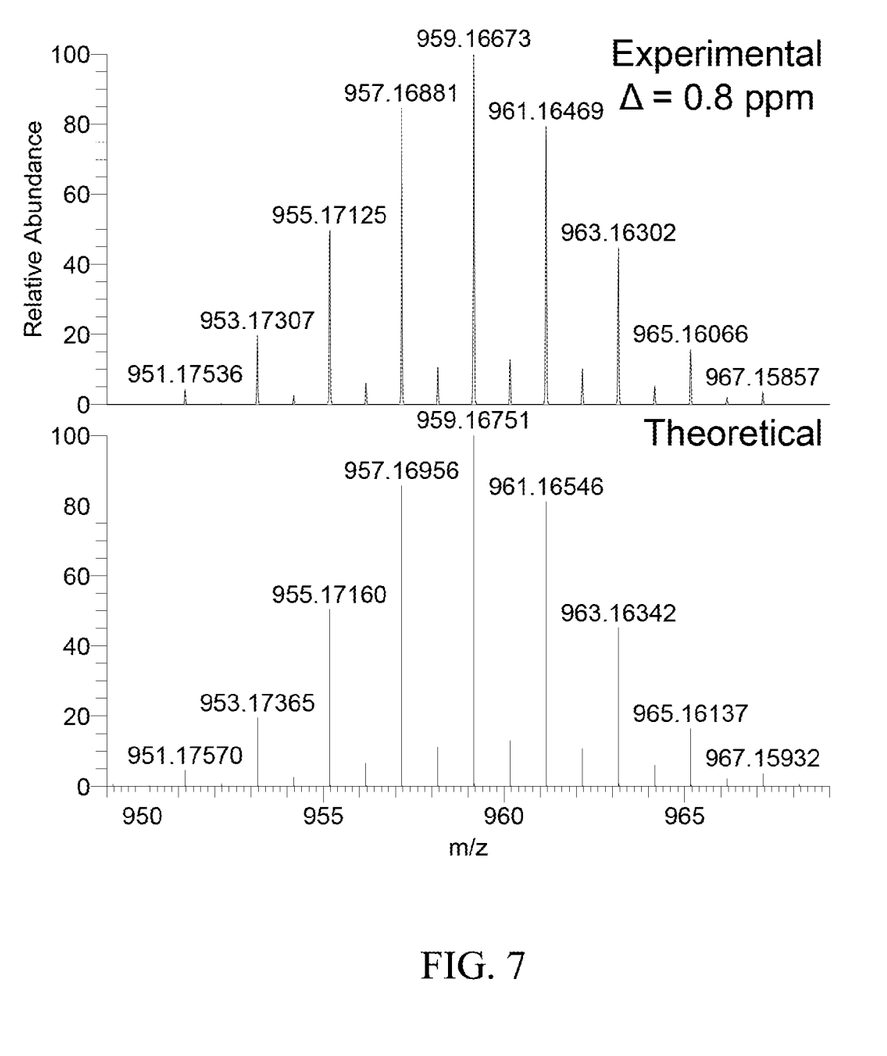
FIG. 7 is an exemplary comparison between a measured and theoretical m/z for a set of high mass ions when calibration includes low mass calibration ions and high mass sample ions.
Figure 8:
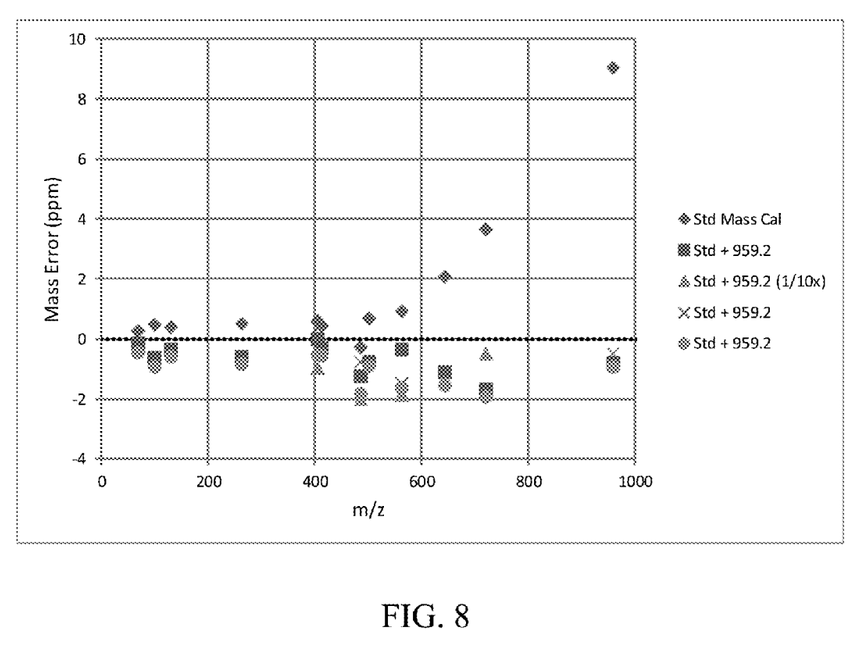
FIG. 8 is an exemplary graph of the mass errors as a function of m/z when calibration includes low mass calibration ions and high mass sample ions.

FIG. 7 shows an experimental mass spectrum of the bromobiphenyl ethers using the calibration derived from the PFTBA calibration compound and decabromobiphenyl ether in the sample as compared to a theoretical mass spectrum of the bromobiphenyl ethers. The error in the experimentally determined mass at m/z 959.16751 is 0.8 ppm. The data are tabulated in Table 2. FIG. 8 is a graph of the mass errors as a function of m/z ratio. FIG. 8 compares the mass error curve from FIG. 6 (mass calibration with PFTBA only) to the mass error curve for multiple runs calibrated using the PFTBA calibration compound and the decabromobphenyl ether within the sample. The mass errors when using both PFTBA and decabromobphenyl ether are relatively consistent across the measured m/z range. Although, the errors tend to be negative and the masses tend to be systematically underestimated for these samples.

TABLE 2

|  | Theoretical m/z | Calculated m/z | Error (ppm) |
|---|---|---|---|
| PFTBA | 68.9946612 | 68.99465 | −0.162331401 |
| PFTBA | 99.9930644 | 99.993 | −0.644044668 |
| PFTBA | 130.9914676 | 130.99142 | −0.363382447 |
| PFTBA | 263.9865576 | 263.9864 | −0.597000095 |
| PFTBA | 413.9769768 | 413.97684 | −0.33045316 |
| PFTBA | 501.9705896 | 501.97021 | −0.756219603 |
| Tribromobiphenyl ether | 405.80211 | 405.80211 | 0 |
| Tetrabromobiphenyl ether | 485.71057 | 485.70997 | −1.235303568 |
| Pentabromobiphenyl ether | 563.62109 | 563.62089 | −0.354848325 |
| Hexabromobiphenyl ether | 643.52955 | 643.52884 | −1.103290439 |
| Heptabromobiphenyl ether | 721.44006 | 721.43883 | −1.704923345 |
| Decabromobiphenyl ether | 959.16751 | 959.16673 | −0.813205193 |
|  |  | RMS (ppm) | 0.818936131 |
|  |  | Max (ppm) | −1.704923345 |

Figure 9:
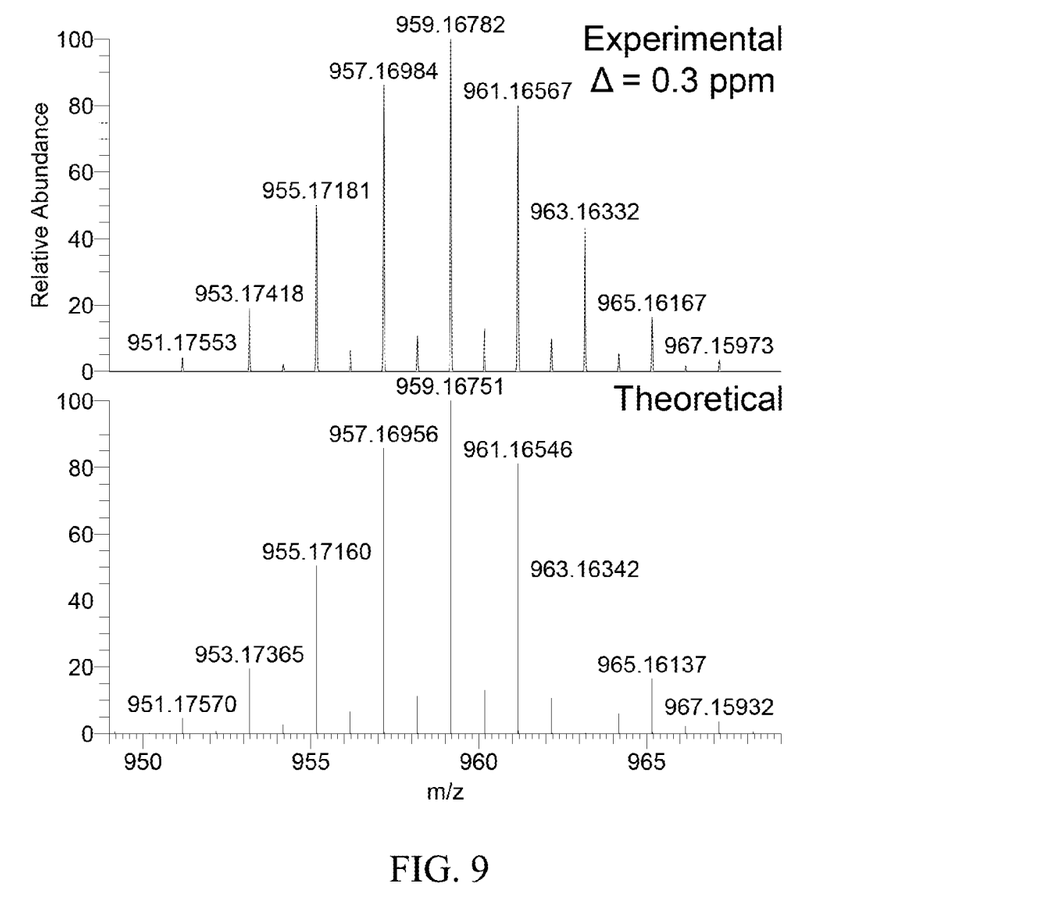
FIG. 9 is an exemplary comparison between a measured and theoretical m/z for a set of high mass ions when calibration includes low mass calibration ions and high mass sample ions with a lock mass.
Figure 10:
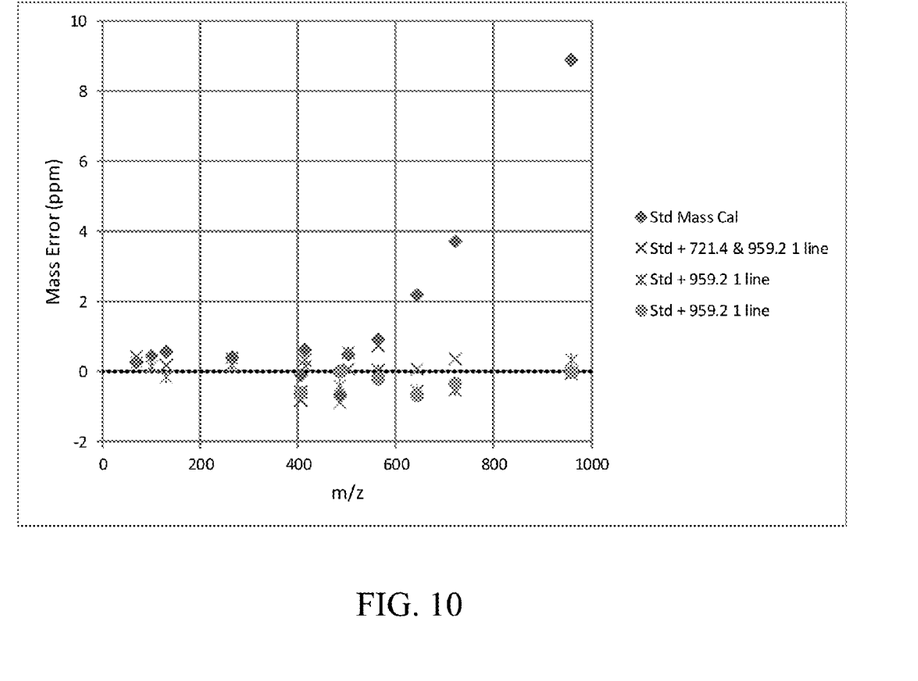
FIG. 10 is an exemplary graph of the mass errors as a function of m/z when calibration includes low mass calibration ions and high mass sample ions with a lock mass.

FIG. 9 shows an experimental mass spectrum of the bromobiphenyl ethers using the calibration derived from the PFTBA calibration compound and decabromobiphenyl ether and using decabromobiphenyl ether as a lock mass as compared to a theoretical mass spectrum of the bromobiphenyl ethers. The error in the experimentally determined mass at m/z 959.16751 is 0.3 ppm. The data are tabulated in Table 3. FIG. 10 is a graph of the mass errors as a function of m/z ratio. FIG. 10 compares the mass error curve from FIG. 6 (mass calibration with PFTBA only) to the mass error curve for multiple runs when the PFTBA calibration compound and the decabromobphenyl ether are used for the calibration curve and decabromobphenyl ether (alone or in combination with Heptabromobiphenyl ether) is used as a lock mass. The mass errors when using both PFTBA and decabromobphenyl ether along with a lock mass are relatively consistent across the measured m/z range.

TABLE 3

|  | Theoretical m/z | Calculated m/z | Error (ppm) |
|---|---|---|---|
| PFTBA | 68.9946612 | 68.99468 | 0.272484851 |
| PFTBA | 99.9930644 | 99.99308 | 0.15601082 |
| PFTBA | 130.9914676 | 130.99145 | −0.134359896 |
| PFTBA | 263.9865576 | 263.98661 | 0.198494955 |
| PFTBA | 413.9769768 | 413.97711 | 0.321757024 |
| PFTBA | 501.9705896 | 501.97086 | 0.538676978 |
| Tribromobiphenyl ether | 405.80211 | 405.80188 | −0.566778719 |
| Tetrabromobiphenyl ether | 485.71057 | 485.71037 | −0.411767856 |
| Pentabromobiphenyl ether | 563.62109 | 563.62111 | 0.035484833 |
| Hexabromobiphenyl ether | 643.52955 | 643.52919 | −0.559414871 |
| Heptabromobiphenyl ether | 721.44006 | 721.43969 | −0.51286312 |
| Decabromobiphenyl ether | 959.16751 | 959.16782 | 0.323196936 |
|  |  | RMS (ppm) | 0.378838198 |
|  |  | Max (ppm) | −0.566778719 |

What is claimed is:

1. A method comprising:
   producing ions from one or more calibrant species and delivering the ions to a mass analyzer;
   measuring a first set of mass related physical values for the ions from the one or more calibrant species;
   producing ions from a sample and delivering the ions to a mass analyzer, the sample including ion species of unknown mass and a first sample ion species of known mass, the first sample ion species having a mass-to-charge ratio outside of the range of the mass-to-charge ratios of the calibrant ion species;
   measuring a second mass related physical value for the first sample ion species;
   calculating a mass calibration curve based on the first set of mass related physical values for the plurality calibrant ion species and second mass related physical value for the first sample ion species; and
   modifying at least one instrument parameter based on the mass calibration curve.

2. The method of claim 1, wherein the mass analyzer includes a Fourier transform mass analyzer.

3. The method of claim 2, wherein the instrument parameter is selected from the group consisting of a coefficient relating m/z to ion frequency, a frequency range for an image current, a digitizing rate, a filter bandwidth for an image current, and any combination thereof.

4. The method of claim 1, wherein the mass analyzer includes a quadrupole mass analyzer or a quadrupole ion trap mass analyzer.

5. The method of claim 4, wherein the instrument parameter is selected from the group consisting of an RF voltage, a DC voltage, and any combination thereof.

6. The method of claim 1, wherein the mass analyzer includes a time-of-flight mass analyzer.

7. The method of claim 6, wherein the instrument parameter is selected from the group consisting of a coefficient relating m/z to flight time, an acquisition time window, a flight tube clearing pulse time, and any combination thereof.

8. The method of claim 1, wherein the sample is provided by a gas chromatographic instrument.

9. The method of claim 1, wherein the sample is provided by a liquid chromatographic instrument.

10. The method of claim 1, further comprising:
providing a second sample to the mass spectrometer, the sample including a second sample ion species;
operating the mass spectrometer using the modified instrument parameter from the calibration; and
measuring a third mass related physical value for the second sample ion species.

11. The method of claim 10, further comprising:
shifting the mass calibration curve based on a measured mass-to-charge ratio of a third sample ion species within the second sample to account for scan specific drifts in the mass calibration curve, wherein the instrument parameter is not changed based on the shifting of the mass calibration curve.

12. The method of claim 10, wherein the second sample ion species has a mass-to-charge ratio within the range of the mass-to-charge ratio of the first sample ion species and the mass-to-charge ratio of at least one of the calibrant ion species.

13. The method of claim 1, wherein the first sample ion species has a mass-to-charge ratio above the range of the mass-to-charge ratios of the calibrant ion species.

14. The method of claim 1, wherein the first sample ion species has a mass-to-charge ratio below the range of the mass-to-charge ratios of the calibrant ion species.

15. A mass spectrometer, comprising:
an ion source configured to form ions from one or more calibrant species and from a sample, the sample including ion species of unknown mass and a first sample ion species of known mass, the first sample ion species having a mass-to-charge ratio outside of the range of the mass-to-charge ratios of the calibrant ion species;
a mass analyzer configured to measure a mass related physical value for an ion;
a controller configured to:
obtain a first set of mass related physical values for ions from the one or more calibrant species;
obtain a second mass related physical value for the first sample ion species;
calculate a mass calibration curve based on the first set of mass related physical values, the second mass related physical value, and known mass-to-charge ratios of the ions from the one or more calibrant species and the first sample ion species; and
modify the operation of the mass analyzer based on the mass calibration curve.

16. The mass spectrometer of claim 15, wherein the mass analyzer includes a Fourier transform mass analyzer.

17. The mass spectrometer of claim 16, wherein modifying the operation of the mass analyzer includes modifying a coefficient relating m/z to ion frequency, a frequency range for an image current, a digitizing rate, a filter bandwidth for an image current, and any combination thereof.

18. The mass spectrometer of claim 15, wherein the mass analyzer includes a quadrupole mass analyzer or a quadrupole ion trap mass analyzer.

19. The mass spectrometer of claim 18, wherein modifying the operation of the mass analyzer includes modifying an RF voltage, a DC voltage, or any combination thereof.

20. The mass spectrometer of claim 15, wherein the mass analyzer includes a time-of-flight mass analyzer.

21. The mass spectrometer of claim 20, wherein modifying the operation of the mass analyzer includes modifying a coefficient relating m/z to flight time, an acquisition time window, a flight tube clearing pulse time, or any combination thereof.

22. The mass spectrometer of claim 15, wherein the mass spectrometer further includes a gas chromatograph for supplying the sample to the ion source.

23. The mass spectrometer of claim 15, wherein the mass spectrometer further includes a liquid chromatograph for supplying the sample to the ion source.

24. The mass spectrometer of claim 15, wherein the controller is further configured to:
operate the ion source to provide a second sample to the mass spectrometer, the sample including a second sample ion species;
operate the mass spectrometer using the modified instrument parameter from the calibration; and
obtain a third set of mass related physical values for the second sample ion species.

25. The mass spectrometer of claim 24, wherein the controller is further configured to:
shift the mass calibration curve based on a measured mass-to-charge ratio of a third sample ion species within the second sample to account for scan specific drift in the mass calibration curve, wherein the operation of the mass analyzer is not changed based on the shifting of the mass calibration curve.

26. The mass spectrometer of claim 15, wherein the first sample ion species has a mass-to-charge ratio above the range of the mass-to-charge ratios of the calibrant ion species.

27. The mass spectrometer of claim 15, wherein the first sample ion species has a mass-to-charge ratio below the range of the mass-to-charge ratios of the calibrant ion species.

* * * * *